US00PP36694P2

(12) United States Plant Patent
Mathey

(10) Patent No.: US PP36,694 P2
(45) Date of Patent: May 20, 2025

(54) ***SYRINGA* PLANT NAMED 'SMNSPWF'**

(50) Latin Name: *Syringa pubescens*
Varietal Denomination: SMNSPWF

(71) Applicant: Megan M. Mathey, Holland, MI (US)

(72) Inventor: Megan M. Mathey, Holland, MI (US)

(73) Assignee: SPRING MEADOW NURSERY, INC., Grand Haven, MI (US)

( * ) Notice: Subject to any disclaimer, the term of this patent is extended or adjusted under 35 U.S.C. 154(b) by 0 days.

(21) Appl. No.: 18/947,758

(22) Filed: Nov. 14, 2024

(51) Int. Cl.
*A01H 6/00* (2018.01)
*A01H 5/02* (2018.01)

(52) U.S. Cl.
USPC ..... Plt./248

(58) Field of Classification Search
USPC ..... Plt./248
CPC ..... A01H 6/00; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Syringa* plant named 'SMNSPWF', characterized by its relatively compact, upright to outwardly spreading and low mounding plant habit; vigorous growth habit; freely branching habit, dense and bushy appearance; freely and remontant flowering habit; inflorescences with fragrant white-colored flowers; and relative resistance to Powdery Mildew.

2 Drawing Sheets

Figure 1:
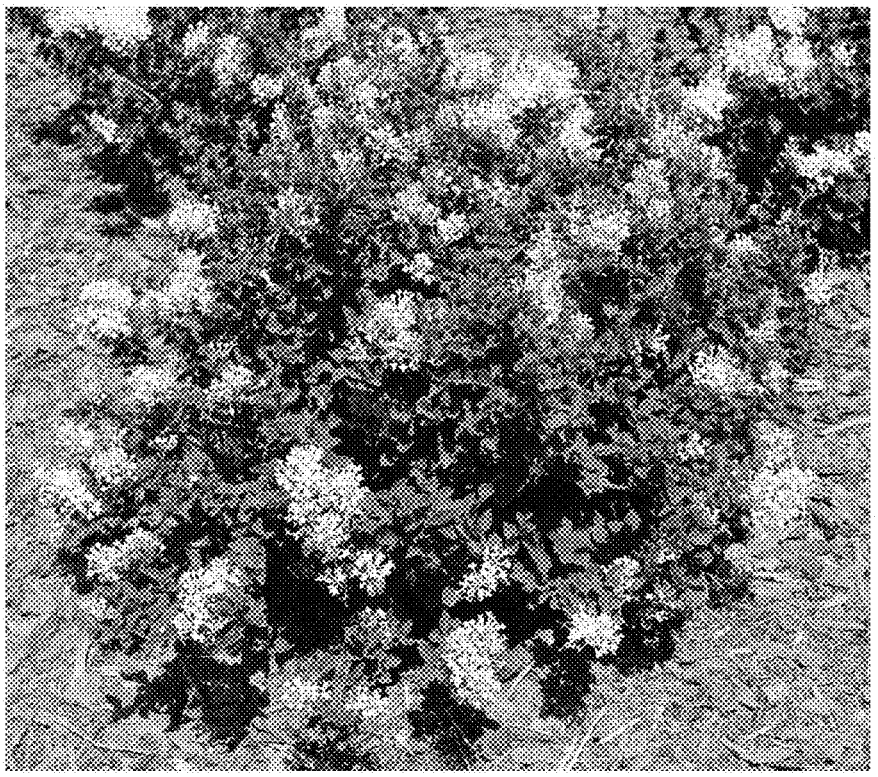

Botanical designation: *Syringa pubescens.*
Cultivar denomination: 'SMNSPWF'.

BACKGROUND OF THE INVENTION

The present invention relates to a new and distinct cultivar of *Syringa* plant, commonly referred to as Lilac, botanically known as *Syringa pubescens* and hereinafter referred to by the name 'SMNSPWF'.

The new *Syringa* plant is a product of a planned breeding program conducted by the Inventor in Grand Haven, Michigan. The objective of the breeding program is to create new compact and freely-flowering *Syringa* plants with attractive flowers and remontant flowering habit.

The new *Syringa* plant originated from an open-pollination during the spring of 2015 of *Syringa pubescens* 'SMNSPTP', disclosed in U.S. Plant Pat. No. 35,123, as the female, or seed, parent with an unknown selection of *Syringa pubescens* as the male, or pollen, parent. The new *Syringa* plant was discovered and selected by the Inventor during the summer of 2018 as a single flowering plant within the progeny of the stated open-pollination in a controlled environment in Grand Haven, Michigan.

Asexual reproduction of the new *Syringa* plant by softwood cuttings in a controlled greenhouse environment in Grand Haven, Michigan since the summer of 2018 has shown that the unique features of this new *Syringa* plant are stable and reproduced true to type in successive generations of asexual reproduction.

SUMMARY OF THE INVENTION

Plants of the new *Syringa* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNSPWF'. These characteristics in combination distinguish 'SMNSPWF' as a new and distinct *Syringa* plant:

1. Relatively compact, upright to outwardly spreading and low mounding plant habit.
2. Vigorous growth habit.
3. Freely branching habit, dense and bushy appearance.
4. Freely and remontant flowering habit.
5. Inflorescences with fragrant white-colored flowers.
6. Relatively resistant to Powdery Mildew.

Plants of the new *Syringa* can be compared to plants of the female parent, 'SMNSPTP'. Plants of the new *Syringa* 1differ primarily from plants of 'SMNSPTP' in the following characteristics:

1. Plants of the new *Syringa* are shorter and broader than and not as upright as plants of 'SMNSPTP'.
2. Flowers of plants of the new *Syringa* are white in color whereas flowers of plants of 'SMNSPTP' are light purple in color.

Plants of the new *Syringa* can be compared to plants of the *Syringa* hybrid 'SMNSDTP', disclosed in U.S. Plant Pat. No. 32,969. In side-by-side comparisons, plants of the new *Syringa* differ primarily from plants of 'SMNSDTP' in the following characteristics:

1. Flower buds of plants of the new *Syringa* are light yellow green in color whereas flower buds of plants of 'SMNSDTP' are dark purple in color.
2. Flowers of plants of the new *Syringa* are white in color whereas flowers of plants of 'SMNSDTP' are light lavender in color.

BRIEF DESCRIPTION OF THE PHOTOGRAPHS

The accompanying colored photographs illustrate the overall appearance of the new *Syringa* plant showing the colors as true as it is reasonably possible to obtain in colored reproductions of this type. Colors in the photographs may differ slightly from the color values cited in the detailed botanical description which accurately describe the colors of the new *Syringa* plant.

The photograph on the first sheet (FIG. 1) is a side perspective view of typical flowering plants of 'SMNSPWF' grown in an outdoor nursery.

Figure 2:
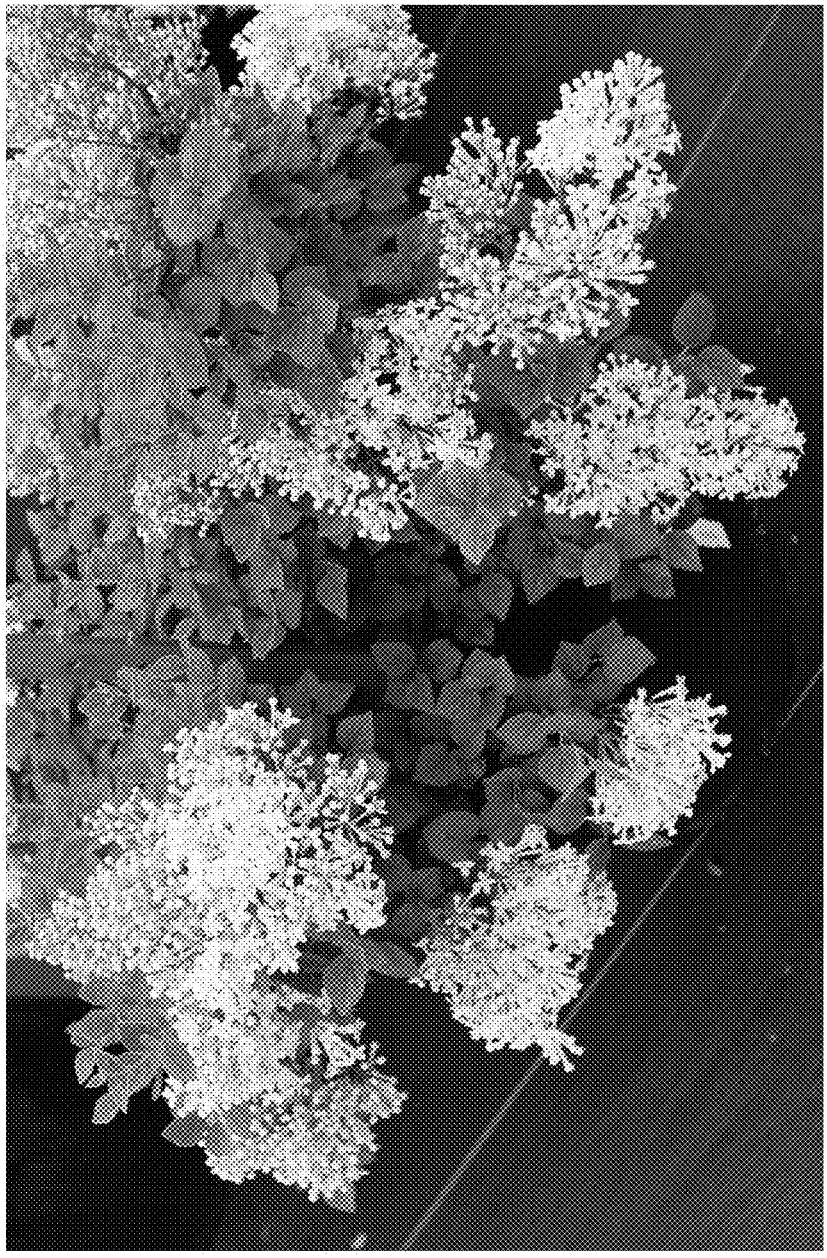

The photograph on the second sheet (FIG. 2) is a close-up view of a typical flowering plant of 'SMNSPWF' grown in a container.

DETAILED BOTANICAL DESCRIPTION

Plants used for the following description were grown during the spring in three-gallon containers in a polyethylene-covered greenhouse and in an outdoor nursery in Grand Haven, Michigan and under cultural practices typical of commercial *Syringa* production. During the production of the plants, day temperatures ranged from 18° C. to 27° C. and night temperatures ranged from 5° C. to 10° C. Plants of the new *Syringa* were three years old when the photographs and description were taken. In the following description, color references are made to The Royal Horticultural Society Colour Chart, 2015 Edition, except where general terms of ordinary dictionary significance are used.

Botanical classification: *Syringa pubescens* 'SMNSPWF'.

Parentage:

- *Female, or seed, parent.*—*Syringa pubescens* 'SMNSPTP', disclosed in U.S. Plant Pat. No. 35,123.
- *Male, or pollen, parent.*—Unknown selection of *Syringa pubescens*, not patented.

Propagation:

- *Type.*—By softwood cuttings.
- *Time to initiate roots, summer.*—About 20 days at temperatures about 18° C. to 27° C.
- *Time to produce a rooted young plant, summer.*—About three months at temperatures about 18° C. to 27° C.
- *Root description.*—Fine, fibrous; typically white in color, actual color of the roots is dependent on substrate composition, water quality, fertilizer, substrate temperature and physiological age of roots.
- *Rooting habit.*—Freely branching; dense.

Plant description:

- *Plant form and growth habit.*—Perennial shrub; relatively compact, upright to outwardly spreading and low mounding plant habit; vigorous growth habit and moderate to rapid growth rate.
- *Branching habit.*—Freely branching habit, dense and bushy appearance; about ten primary lateral branches develop per plant.
- *Plant height.*—About 47.2 cm.
- *Plant diameter* (*area of spread*).—About 58 cm.

Lateral branch description:

- *Length.*—About 34.8 cm.
- *Diameter.*—About 5 mm.
- *Internode length.*—About 1 cm.
- *Aspect.*—About 30° to 60° from vertical.
- *Strength.*—Strong; when woody, rigid.
- *Texture.*—Initially slightly pubescent becoming smooth and glabrous and eventually woody with development.
- *Color, developing.*—Close to 146B to 146C.
- *Color, developed.*—When woody, close to 197C to 197D.

Leaf description:

- *Arrangement.*—Opposite, simple.
- *Length.*—About 1.75 cm.
- *Width.*—About 1.5 cm.
- *Shape.*—Ovate.
- *Apex.*—Broadly acute.
- *Base.*—Obtuse.
- *Margin.*—Entire.
- *Texture, upper and lower surfaces.*—Pubescent.
- *Venation pattern.*—Pinnate.
- *Color.*—Developing and fully expanded leaves, upper surface: Close to NN137C; venation, close to 147B. Developing and fully expanded leaves, lower surface: Close to 147B; venation, close to 147B.
- *Petioles.*—Length: About 3 mm. Diameter: About 1 mm. Texture, upper and lower surfaces: Slightly pubescent. Color, upper and lower surfaces: Close to 146B to 146C.

Flower description:

- *Flower arrangement and flowering habit.*—Single salverform flowers arranged in dense terminal panicles; freely flowering habit with usually about 200 flowers developing per inflorescence; flowers face mostly upright to outwardly depending on position on inflorescence.
- *Natural flowering season and flower longevity.*—Flowering remontant; plants of the new *Syringa* flower during the spring (April), during the summer (June) and then again in the autumn (September) in Michigan; individual flowers last about two weeks on the plant, flowers not persistent.
- *Fragrance.*—Strongly fragrant; fragrance sweet, floral and pleasant with notes of jasmine and orange blossom.
- *Flower buds* (*before showing color*).—Length: About 1 cm. Diameter: About 2 mm. Shape: Spatulate. Color: Close to 145C.
- *Inflorescence height.*—About 6.5 cm.
- *Inflorescence diameter.*—About 6 cm.
- *Flower diameter.*—About 1 cm.
- *Flower depth.*—About 1.5 cm.
- *Flower throat diameter.*—About 2 mm.
- *Flower tube length.*—About 1.5 cm.
- *Flower tube diameter, proximally.*—About 1 mm.
- *Petals.*—Quantity and arrangement: Single whorl of four petals; lower portion of petals fused forming a narrow tube. Lobe length: About 4 mm. Lobe width: About 3 mm. Lobe shape: Elliptic. Lobe apex: Acute. Lobe margin: Entire. Lobe texture, upper and lower surfaces: Smooth, glabrous; soft, silky. Texture, throat and tube: Smooth, glabrous. Color: When opening, upper and lower surfaces: Close to 155A. Fully opened, upper and lower surfaces: Close to NN155B; color does not change with subsequent development. Throat: Close to NN155B. Tube: Close to NN155B.
- *Sepals.*—Quantity and arrangement: Single whorl of four small inconspicuous sepals; fused towards the base forming a campanulate-shaped calyx. Length: Less than 1 mm. Width: Less than 1 mm. Shape: Narrowly deltoid. Apex: Acute. Margin: Entire. Texture, upper and lower surfaces: Smooth, glabrous. Color, upper and lower surfaces: Close to 144A to 144B.

*Peduncles*.—Length: About 4.5 cm. Diameter: About 2 mm. Strength: Strong. Aspect: About 45° to 90° from the stem axis. Texture: Smooth, glabrous. Color: Close to 197C to 197D.

*Pedicels*.—Length: About 5 mm. Diameter: About 1 mm. Strength: Strong, somewhat flexible. Aspect: About 45° from peduncle axis. Texture: Smooth, glabrous. Color: Close to 144A.

*Reproductive organs*.—Androecium: Quantity of stamens per flower: Two; filaments are adnate to the throat. Anther size: About 1 mm by 2 mm. Anther shape: Oblong. Anther color: Close to 8A. Amount of pollen: Moderate. Pollen color: Close to 8D. Gynoecium: Quantity of pistils per flower: One. Pistil length: About 3 mm. Stigma shape: Oblong. Stigma color: Close to NN155B. Style length: About 3 mm. Style color: Close to NN155B. Ovary color: Close to 144A.

*Seeds and fruits*.—To date, seed and fruit development have not been observed on plants of the new *Syringa*.

Garden performance: Plants of the new *Syringa* have been observed to have good garden performance and to tolerate rain, wind and temperatures ranging from about −31 C to about 38° C.

Pathogen & pest resistance: Plants of the new *Syringa* have been observed to be relatively resistant to Powdery Mildew (*Erysiphe syringae*). To date, plants of the new *Syringa* have not been observed to be resistant to pests and other pathogens common to *Syringa* plants.

It is claimed:

1. A new and distinct *Syringa* plant named 'SMNSPWF' as herein illustrated and described.

* * * * *